United States Patent [19]

Harris et al.

[11] Patent Number: 4,967,767
[45] Date of Patent: Nov. 6, 1990

[54] VAGINAL SHIELD FOR PREVENTING SEXUALLY TRANSMITTED DISEASES

[76] Inventors: Robert L. Harris, 16500 Patton St.; Johnnie Carter, 19757 Edinborough, both of Detroit, Mich. 48219

[21] Appl. No.: 388,803

[22] Filed: Aug. 3, 1989

[51] Int. Cl.$^5$ .............................. A61F 13/00
[52] U.S. Cl. ................... 128/844; 128/830; 128/917; 128/918
[58] Field of Search .......... 128/842, 843, 844; 604/347, 349, 352, 353; 2/111, 227, 406, 403, 405, 408

[56] References Cited

U.S. PATENT DOCUMENTS

| | | | |
|---|---|---|---|
| 1,123,994 | 1/1915 | Cranston | 128/835 |
| 2,123,343 | 7/1938 | Rightsell | 2/21 |
| 3,536,066 | 10/1970 | Ludwig | 128/843 |
| 3,905,372 | 9/1975 | Denkinger | 128/285 |
| 4,022,213 | 5/1977 | Stein | 604/353 |
| 4,031,897 | 6/1977 | Graetz | 128/286 |
| 4,664,104 | 5/1987 | Jaicks | 128/844 |
| 4,840,624 | 6/1989 | Lee | 604/349 |

FOREIGN PATENT DOCUMENTS

| | | | |
|---|---|---|---|
| 1158507 | 12/1983 | Canada | 604/349 |
| 2606275 | 5/1988 | France | 604/349 |
| 117234 | 10/1926 | Switzerland | 604/349 |

Primary Examiner—Robert A. Hafer
Assistant Examiner—Charles H. Sam
Attorney, Agent, or Firm—Robert G. Mentag

[57] ABSTRACT

A shield appliance including a shield support strap structure that fits over the lower end of a female user, and a non-porous, elastic shield member, detachably carried by the support strap member, detachably carried by the support strap structure, and positioned over the perineal area of the female use to protect against vaginal contact, and prevent the spread of sexually transmitted diseases, during cunnilingus.

1 Claim, 1 Drawing Sheet

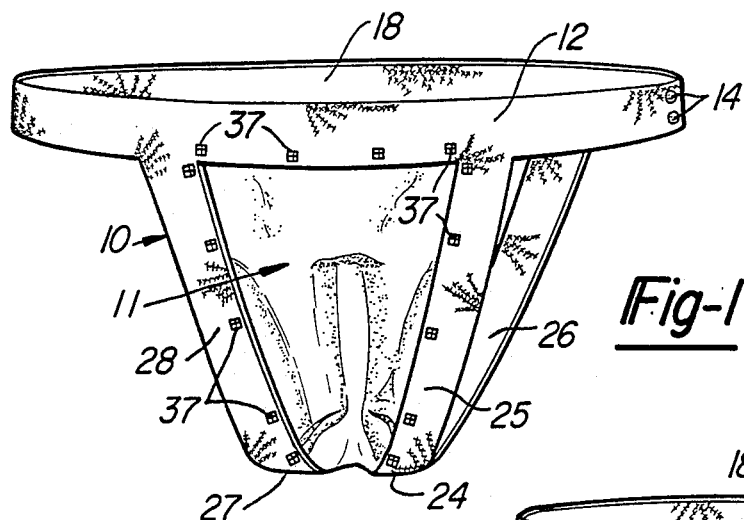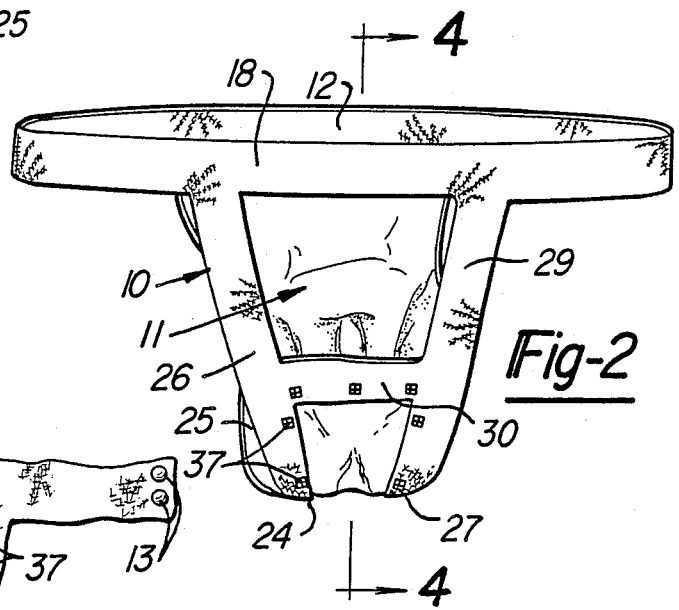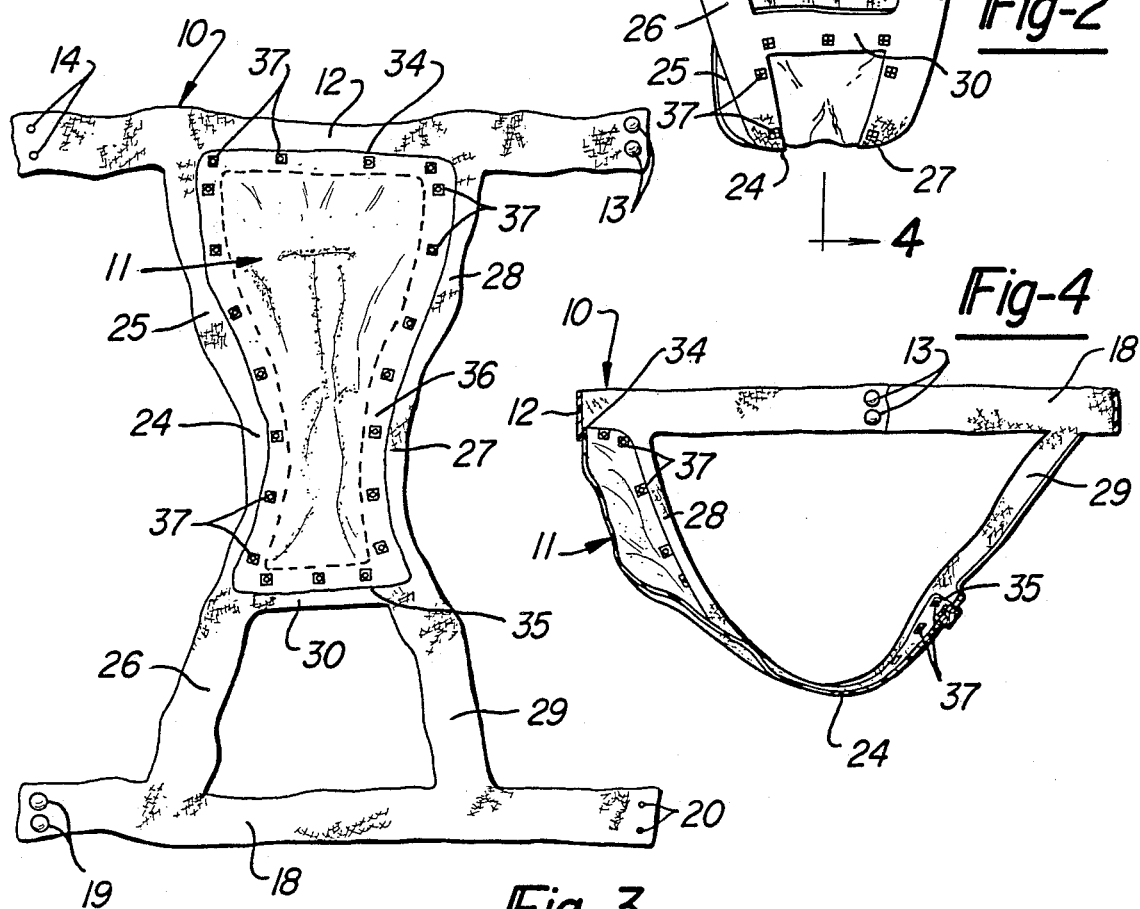

VAGINAL SHIELD FOR PREVENTING SEXUALLY TRANSMITTED DISEASES

BACKGROUND OF THE INVENTION

1. Technical Field

The field of art to which this invention pertains may be generally located in the class of devices relating to prophylactic devices. Class 128, Surgery, Sub-Class 132, United States Patent Office Classification, appears to be the applicable general area of art to which the subject matter similar to this invention has been classified in the past.

2. Background Information

It is known in the prophylactic art to provide condoms for the prevention of venereal infection during coitus. Some of the prior art condoms have been carried on supporting garments, as shown in U.S. Pat. Nos.:
Ludwig 3,536,666 issued Oct. 17th, 1970
Jaicks 4,664,104 issued May 12th, 1987
A disadvantage of the aforementioned devices is that they are not capable of permitting cunnilingus, while also preventing the transmission of sexual disease.

SUMMARY OF THE INVENTION

In accordance with the present invention, a vaginal shield is provided which assists in preventing the spread of sexually transmitted diseases during cunnilingus. The vaginal shield includes a support means which comprises a body encircling support member which carries a pair of left and right support straps that extend from the front side of the support member downwardly and through the crotch of a person wearing the vaginal shield, and thence upwardly and to a fixed engagement with the rear side of the support member. A shield member is detachably carried by the support means and completely covers the vagina, and it extends downwardly and under the crotch of the person wearing the shield and thence upwardly to cover the anus, so as to cover the entire perineal area. The vagina shield is made of a suitable non-porous, latex rubber of a thickness which will not allow sexually transmitted organisms to permeate its wall during use of the shield. The shield allows access to the female genitalia while preventing the exchange of body secretions, that is saliva and vaginal secretions, both of which could contain sexually transmitted disease organisms. The vagina shield is designed for a one time use only.

BRIEF DESCRIPTION OF THE DRAWING

FIG. 1 is a front elevation view of a vagina shield appliance, made in accordance with the principles of the present invention.

FIG. 2 is a rear elevation view of the vagina shield illustrated in FIG. 1.

FIG. 3 shows the vagina shield appliance in a spread out, flat, disposition and in a condition before the vagina shield is put on the body of a female user.

FIG. 4 is an elevation section view of the shield structure shown in FIG. 3, taken along the line 4—4 thereof, and looking in the direction of the arrows.

DESCRIPTION OF THE PREFERRED EMBODIMENT

Referring now to the drawing and in particular to FIGS. 1—4, the numeral 10 generally designates a vaginal shield support means which detachably carries a vaginal shield, generally indicated by the numeral 11.

As best seen in FIG. 3, the support means 10 includes a body encircling support member in the form of a belt means comprising a front belt portion 12 and a rear belt portion 18. Belt portions 12 and 18 may be made from any suitable material as for example, from an elastic material. The front and rear belt portions 12 and 18 are detachably connected by any suitable means, as by double face buttons indicated by the female portions 13 and 19, and the male portions 14 and 20 of such type buttons.

The vaginal shield support means 10 further includes a left shield supporting strap comprising the middle portion 24, the front portion 25, and the rear portion 26, and a right shield supporting strap comprising the middle portion 27, the front portion 28, and the rear portion 29. The last mentioned left and right shield supporting straps are interconnected by an integral transverse strap 30. As best seen in FIG. 3, the aforementioned left shield supporting strap, the right shield supporting strap and the transverse strap 30 are all integrally connected, with the upper ends of the front strap portions 25 and 28 being integrally attached to the front belt portion 12, and the upper ends of the rear strap portions 26 and 29 being integrally connected to the rear belt portion 18. The left and right shield supporting straps and the transverse strap 30 are preferably, integrally formed with the front and rear belt portions 12 and 18, but it will be understood that these supporting strap portions may be independently formed and attached together to form a supporting structure to carry out the same function as the supporting structure illustrated in FIG. 3. The vaginal shield support means 10 and its aforedescribed parts is made of a heavier material than the vaginal shield 11. It is preferable to use material for the support means 10 that is washable and intended for multiple use, after appropriate disinfecting. On the other hand, the vaginal shield 11 is intended to be discarded after each use. As shown in FIG. 3, the middle portions 24 and 27 of the left and right supporting straps, respectively, curve inwardly for easy passage through the crotch of a user. The left and right shield supporting strap portions 26 and 29 are adapted to be positioned against the buttocks of a user.

As shown in FIG. 3, the vaginal shield 11 is shaped to conform to the shape of the left and right supporting shield straps and it is detachably connected to said straps by a plurality of suitable snap fasteners in the form of double faced buttons 37. As shown in FIG. 3, the upper end 34 of the shield 11 is detachably connected to the front belt portion 12, and the lower end 35 is detachably secured to the transverse strap 30. The lower end 36 of the front portion passes underneath the crotch of a user. The shield 11 is made to cover the perineal area of a user. That is, it is designed to cover the vagina, inclusive of the labia majora, while extending backward and upward over the anus. Its principle purpose however, is coverage of the vagina. The shield 11 is made from a suitable non-porous, latex which will not allow sexually transmitted organisms to permeate its wall during use. A preferable latex is one which is approximately 38,000 millimicrons thick.

As shown in FIG. 3, the supporting belt and strap structure is substantially X-shaped in plan view, and it provides a supporting means to hold the shield 11 snug in the inguinal creases for sealing purposes around the outer labia. As shown in FIGS. 1-4, the shield 11 is made in a loose form to provide excess material over the vagina to permit invagination at that area.

It will be seen that the shield 11 functions as a mechanical barrier in a simple, safe and sanitary manner, without harming human physical sensitivity and health.

What is claimed is:

1. A shield appliance adapted to be worn by a female partner to protect against vaginal contact, and prevent the spread of sexually transmitted diseases, during cunnilingus, comprising:
   (a) a shield support means adapted to be worn by a female user and, including a body encircling belt means, a pair of spaced apart shield member supporting straps that are integrally attached to the belt means and which extend from the belt means at the front of a female user and down through the crotch of the female user and up the rear of the female user to the belt means at the rear of the female user, and an integral transverse supporting strap interconnecting said pair of supporting straps at the rear side of the female user to support the shield member at the anus; and,
   (b) a disposable non-porous, elastic shield member detachably connected to said shield support means and extending over the vaginal area and anus of the female user.

* * * * *